(12) United States Patent
Lyles

(10) Patent No.: US 8,455,377 B2
(45) Date of Patent: Jun. 4, 2013

(54) METHODS OF MAKING CERAMIC AND METAL COMPOSITIONS

(75) Inventor: Mark B. Lyles, Great Lakes, IL (US)

(73) Assignee: Materials Evolution and Development, Exeter, RI (US)

(*) Notice: Subject to any disclaimer, the term of this patent is extended or adjusted under 35 U.S.C. 154(b) by 705 days.

(21) Appl. No.: 12/370,378

(22) Filed: Feb. 12, 2009

(65) Prior Publication Data
US 2009/0148592 A1 Jun. 11, 2009

Related U.S. Application Data

(63) Continuation of application No. 11/233,815, filed on Sep. 23, 2005, now abandoned, which is a continuation-in-part of application No. 09/817,010, filed on Mar. 24, 2001, now Pat. No. 7,011,841, and a continuation of application No. 10/626,005, filed on Jul. 24, 2003, now abandoned.

(60) Provisional application No. 60/192,112, filed on Mar. 24, 2000.

(51) Int. Cl.
*C03C 10/00* (2006.01)

(52) U.S. Cl.
USPC .......................................................... 501/2

(58) Field of Classification Search
USPC .......................................................... 501/2
See application file for complete search history.

(56) References Cited

U.S. PATENT DOCUMENTS

| | | | |
|---|---|---|---|
| 3,983,270 A | 9/1976 | Licari et al. | 427/372 |
| 4,753,856 A * | 6/1988 | Haluska et al. | 428/698 |
| 5,560,960 A | 10/1996 | Singh et al. | 427/222 |
| 5,614,043 A | 3/1997 | Ritland et al. | 156/89 |
| 5,618,475 A | 4/1997 | Johnson et al. | 264/10 |
| 5,621,035 A | 4/1997 | Lyles et al. | 524/404 |
| 5,629,186 A | 5/1997 | Yasukawa et al. | 435/177 |
| 5,772,754 A | 6/1998 | Tanaka et al. | 117/5 |
| 5,780,281 A | 7/1998 | Yasukawa et al. | 435/176 |
| 5,843,767 A | 12/1998 | Beattie | 435/287.1 |
| 5,951,295 A | 9/1999 | Lyles et al. | 433/228.1 |
| 5,964,745 A | 10/1999 | Lyles et al. | 604/891.1 |
| 6,063,395 A | 5/2000 | Markkula et al. | 424/422 |
| 6,262,129 B1 | 7/2001 | Murray et al. | 516/33 |
| 6,291,547 B1 | 9/2001 | Lyles et al. | 523/116 |
| 6,346,136 B1 | 2/2002 | Chen et al. | 75/343 |
| 6,391,494 B2 | 5/2002 | Reitz et al. | 429/219 |
| 6,472,459 B2 | 10/2002 | Morales et al. | 524/439 |
| 6,544,324 B1 | 4/2003 | Lyles et al. | 106/35 |
| 6,635,339 B1 * | 10/2003 | Adler et al. | 428/307.7 |
| 2001/0044159 A1 | 11/2001 | Lyles | 436/527 |
| 2002/0041932 A1 | 4/2002 | Ogawa | 427/376.2 |

OTHER PUBLICATIONS

Kim et al. "Size-Monodisperse Metal Nanoparticles via Hydrogen-Free Spray Pyrolysis." Advanced Materials, vol. 14, No. 7; pp. 518-521 (4 pages), Apr. 4, 2002.

* cited by examiner

*Primary Examiner* — Paul Dickinson
(74) *Attorney, Agent, or Firm* — King & Spalding L.L.P.

(57) ABSTRACT

A novel metal/ceramic hybrid material in which the void space of the ceramic is filled with metal. The metal may be bonded to the ceramic, for example by formation of a metal oxide. The metal may be introduced into the ceramic as small particles in a suspension then heated to melt the metal, allowing bonding to the ceramic or better filling of the void space. The hybrid material may be used in a variety of applications.

19 Claims, 1 Drawing Sheet

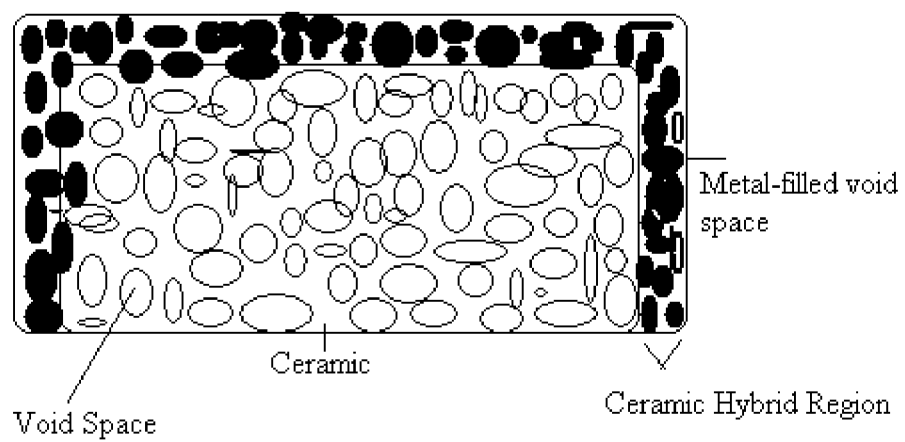

METHODS OF MAKING CERAMIC AND METAL COMPOSITIONS

CROSS-REFERENCE TO RELATED APPLICATIONS

The present application is a continuation under 35 U.S.C. §120 of U.S. application Ser. No. 11/233,815 filed on Sep. 23, 2005 now abandoned, which is a continuation-in-part of U.S. application Ser. No. 09/817,010 filed on Mar. 24, 2001 now U.S. Pat. No. 7,011,841 which is a non-provisional application of U.S. Provisional Application Serial No. 60/192,112, filed on Mar. 24, 2000 and which is also a continuation of U.S. application Ser. No. 10/626,005 filed on Jul. 24, 2003 now abandoned, all of which are incorporated by reference herein.

FIELD OF THE INVENTION

The present invention relates to compositions containing both metal and ceramic as well as methods of making and using such compositions. Specifically, it relates to a silica ceramic containing a metal within the void space formed by introducing metal particles into the void space.

BACKGROUND

Hybrid materials including both metals and ceramics have traditionally been difficult to form and have also been plagued with durability problems. Many of these problems result from difficulties in filling void space within ceramics with a metal and with stable bonding between the metal and the ceramic.

Some such metal/ceramic hybrid materials for use in dentistry are described in U.S. Pat. No. 5,621,035. Specifically, the '035 patent describes filler compositions and ceramic enhanced dental materials. In one embodiment, the filler composition and the ceramic dental restorative material are comprised of about 22% by weight alumina, about 78% by weight silica, about 2% by weight silicon carbide, and about 2.85% by weight boron nitride with less than 1% cristobalite contamination. This material is porous and may be used in combination with metal amalgams.

Another porous ceramic material for use in dentistry is described in U.S. Pat. No. 5,951,295. The '295 Patent describes ceramic fused fiber enhanced dental materials, such as materials comprising from about 1% to about 50% by weight alumina, from about 50% to about 98% silica, and from about 1% to about 5% by weight boron.

Another similar ceramic is also described in U.S. Pat. No. 5,964,745 which describes an implantable system for bone or vascular tissue. The system comprises porous, linked fibrous biomaterial manufactured from nonwoven, randomly-oriented fibers linked together using a fusion source at a plurality of cross-points into a porous structure, the biomaterial having a plurality of voids of a predetermined mean void size effective for stimulating angiogenesis in said biomaterial from the tissue or bone.

Yet another porous ceramic material has been described in Yasukawa et al. in U.S. Pat. Nos. 5,629,186 and 5,780,281. A composite was prepared from silica and/or alumina fibers with added boron nitride.

Although attempts have been made to combine metals with ceramics, hybrid materials able to capitalize on the beneficial properties of both ceramics and metals still require additional development.

SUMMARY OF THE INVENTION

The present invention relates to a hybrid material including a ceramic with void space and a metal covalently bonded to the ceramic.

In a specific embodiment, the ceramic includes silica. In more specific embodiments, the ceramic is 100% silica and may contain up to 50% cristobalite, or it may include up to 60% alumina.

In specific embodiments, the metal may be Mg, Ca, Sc, Ti, Cr, Mn, Fe, Co, Ni, Cu, Zn, Pd, Ag, Cd, Pt, Au, any ionic forms thereof, and any combinations thereof or an alloy. The metal may occupy at least 50%, 60%, 70%, 80%, 90%, 95% or 98% or other percentages of the void space. The metal may also occupy at least 50% of the hybrid material by volume or weight.

The invention also includes a method of making a hybrid material, including any of the hybrid materials described above, by providing a ceramic with void space, introducing metal particles into the void space of the ceramic and heating the metal particles so that the ceramic is covalently bonded to the metal after the heating step.

In specific embodiments, the metal particles are heated by supplying an electric current to the metal particles. The ceramic may include exposed surfaces with at least 50% silicon dioxide prior to introducing the metal particles. It may also includes exposed surfaces with titanium dioxide or platinum oxide prior to introducing the metal particles.

In other specific embodiments, the metal particles may be microparticles or nanoparticles. The metal particles may have an average diameter less than the average pore size of the ceramic. More specifically, the metal particles may have an average diameter no greater than two thirds the average pore size of the ceramic.

In specific embodiments of the method, the metal particles may be introduced into the void space by introducing a suspension of metal particles into the ceramic. For example, the suspension of metal particles may include alcohol, water or a combination thereof.

The metal particles may be heated in any appropriate fashion, including by application of an electric current or by convection heating.

For a more complete understanding of the present invention and the advantages thereof, reference is now made to the following drawings and description.

BRIEF DESCRIPTION OF THE DRAWING

FIG. 1 is a schematic cross-section view of a hybrid material including hybrid and non-hybrid regions according to an embodiment of the present invention.

DETAILED DESCRIPTION

The present invention relates to metal/ceramic hybrid materials in which the void space is filled with metal including hybrid materials in which the void space is partially or substantially filled with metal. It also includes methods of making such materials using metal particles.

The ceramic used in the present invention may be any porous ceramic. Ceramics may be selected based upon the properties they are expected to contribute to the completed hybrid material. Ceramics may also be selected based upon their ability to bond to metal.

In specific embodiments of the present invention, the ceramic is a porous material prepared as described in U.S. Pat. Nos. 5,951,295; 5,964,745; 5,621,035; 5,629,186; and 5,780,281. More specifically, the ceramic may be P.R.I.M.M.® (Polymeric Rigid Inorganic Matrix Material), marketed by Materials Evolution & Development U.S.A., Inc. of San Antonio, Tex.

The ceramic portion of the hybrid material of the present invention may be formed using any available methods. The ceramic portion may be formed in such a way as to facilitate introduction of metal particles or it may be formed or treated to increasing bonding of the metal to the ceramic.

Similarly various metal particles may be used to form the metal component of metal/ceramic hybrid materials of the present invention. The metals themselves may be pure metals, alloys, or other combinations of metals. They may be selected based upon the desired properties of the hybrid material. They may also be selected based upon availability of appropriate sized particles or ease of particle formation. In specific embodiments articles may be microparticles or nanoparticles.

The metal particles may be formed or treated in any way, including methods to facilitate introduction of the particles into the ceramic or bonding between the ceramic and the metal. Processes for forming suitable nanoparticles that may be used in specific embodiments of the invention are described in U.S. Pat. Nos. 6,346,136; 5,772,754; 6,472,459; 6,391,494; 6,262,129; 5,618,475; and 5,560,960 and in Kim et al., *Advanced Materials* 14 (7): 518-521 (2002). Similar processes are known for formation of microparticles.

Small metal particles, such as nanoparticles and microparticles, due to their extremely small size, are able to infiltrate very small porous areas of a ceramic. Once metal particles have physically filled a portion of the void space in the ceramic, they may be melted to form the finished hybrid material. Melting may be accomplished by supplying an electric current or through conduction heating. Metal particles may be selected or treated to facilitate bonding with the ceramic. For instance, metals that readily form oxides, such as iron, may be used.

Ceramic portions of the hybrid materials of the present invention may have a variety of densities, which may be reflective of the amount of void space in the ceramic without the metal. In specific embodiments, the ceramic portions have densities of 6 pounds per cubic foot (96.1 kg/m$^3$) and higher, about 8 pounds per cubic foot (128 kg/m$^3$) and higher, about 12 pounds per cubic foot (192 kg/m$^3$) and higher, about 24 pounds per cubic foot (384 kg/m$^3$) and higher, about 36 pounds per cubic foot (577 kg/m$^3$) and higher, about 48 pounds per cubic foot (769 kg/m$^3$) and higher, or about 64 pounds per cubic foot (1025 kg/m$^3$) and higher. Lower density ceramics may be able to be filed with higher proportions of metal. Therefore, the density of the ceramic may influence the metal proportion of the resulting hybrid material and thus the properties of the hybrid material.

The walls of the porous ceramic material range from 0.01 to 2 cm in thickness in specific embodiments of the invention.

The ceramic portions of the hybrid materials in specific embodiments can comprise up to about 100% silica, or up to about 60% alumina. The silica can be up to about 50% cristobalite, up to about 75% cristobalite, up to about 90% cristobalite, up to about 95% cristobalite, up to about 99% cristobalite, or can be about 100% cristobalite. The alumina can be aluminum borosilicate. These variations in composition may affect various properties of the ceramic and the properties of the hybrid material from which it is formed.

The exposed surface of the ceramic portions of the hybrid materials ("surface chemistry") prior to addition of metal can be at least about 50% silicon dioxide, at least about 75% silicon dioxide, at least about 90% silicon dioxide, at least about 95% silicon dioxide, at least about 99% silicon dioxide, or can be about 100% silicon dioxide. Increasing amounts of silicon dioxide on the ceramic surface may increase the level of bonding between the ceramic and metal in the hybrid material.

The ceramic portion of the hybrid material can comprise other oxides in addition to or in place of the silica. For example, titanium dioxide or platinum oxide can be incorporated into the materials.

The metal may bond to the ceramic through reaction with the oxygen of silicon dioxide to form a metal oxide. The amount of bonding may be controlled by proportions of silicon dioxide or other oxides in the ceramic. The reactivity of these oxides with the metal supplied and the nature of the metal supplied will also affect the number and strength of bonds between the metal and ceramic. Other modifications of the ceramic to allow metal bonding are possible and may be accomplished by altering the composition of the ceramic before its formation or by chemical treatment after its formation.

In certain embodiments, the mean pore diameter of the ceramic material may be less than 0.01 microns, about 0.1 micron to about 5 microns, up to about 10 microns, up to about 20 microns, up to about 30 microns, up to about 40 microns, up to about 50 microns, up to about 100 microns, up to about 200 microns, up to about 300 microns, up to about 400 microns, up to about 500 microns, or up to about 1000 microns. Ranges of pore diameter include about 0.1 microns to about 1 micron, about 5 microns to about 10 microns, about 20 microns to about 50 microns, about 100 to about 400 microns, or about 200 microns to about 1000 microns. Smaller pore size may influence the proportion of the void space of the ceramic filled by metal in the hybrid material. In some embodiments of the invention, very large pore sizes, up to several centimeters in diameter, may be appropriate. For example, tank armor may have large pores.

The size of the metal particles may be chosen to allow movement of the metal particles into the ceramic through the pores. Smaller particles will generally enter more readily. Also, smaller particles, once in the ceramic, may be able to more closely pack in the void space and fill a larger portion of it. In specific embodiments, between 1% and 99% of the void space may be filled with metal. In selected embodiments of the present invention, at least 80% of the void space in the ceramic is filled with metal in the hybrid material. In other embodiments at least 85%, 90% or 95% of the void space may be filled with metal. In some embodiments even 99% of the void space may be filled. The amount of void space filled may influence various properties of the resulting hybrid material. For instance, it may influence the proportion of metal to ceramic in the hybrid material. Materials may also be designed so that gas or liquid may flow through the hybrid material.

Materials of the present invention additionally include ceramics in which a portion includes hybrid material, while another portion of the same ceramic is not a hybrid material. For instance, a ceramic may be coated with hybrid material. See FIG. 1.

The metal particles may be introduced into the ceramic through use of a suspension agent, by gas phase deposition, by electroplating or by bonding, for example with organic bonding agents inter alia. For example, metal particles may be suspended in water or alcohol and then allowed to flow into the ceramic. When the suspension agent is slowly removed from the ceramic, the particles remain. For example, a dense layer of particles in the lower portion of the ceramic may be obtained by gradually draining the suspension agent from the ceramic. Metal particles may then be melted, for instance by application of an electric current or convection heating.

Hybrid materials of the present invention have a wide variety of uses including, but not limited to dental amalgams, insulating materials, roofing, catalytic converters, batteries, prosthetics, dental applications, armor, surgical instruments, gears and wear-resistant mechanical parts, and light weight bullets.

The following examples are provided only to illustrate certain aspects of the invention and are not intended to embody the total scope of the invention or any aspect thereof. Variations of the exemplary embodiments of the invention below will be apparent to one skilled in the art and are intended to be included within the scope of the invention.

EXAMPLES

Example 1

Preparation of Ceramic Portion of Hybrid Materials

The preparation of some ceramics suitable for use as the ceramic portions of hybrid materials of the present invention is generally described in U.S. Pat. No. 5,951,295 (issued Sep. 14, 1999) and U.S. Pat. No. 6,291,547 (issued Sep. 18, 2002).

Ceramics can be prepared from: (1) from about 1% to about 50% by weight alumina; (2) from about 50% to about 98% by weight silica; and (3) from about 1% to about 5% by weight boron. In addition, the composition can further comprise silicon carbide up to about 3% by weight. The ceramics can comprise over 99% silica.

Generally, the process for preparing the ceramics can comprise the following steps (as described in U.S. Pat. No. 5,951,295):
(1) preparation of a slurry mixture comprised of pre-measured amounts of purified fibers/materials and deionized water;
(2) removal of shot from slurry mixture;
(3) removal of water after thorough mixing to form a soft billet;
(4) addition of a ceramic binder after the formation of the billet;
(5) placement of the billet in a drying microwave oven for moisture removal; and
(6) sintering the dry billet in a large furnace at about 1600° F. or above.

The high purity silica fibers above are first washed and dispersed in hydrochloric acid and/or deionized water or other solvents. The ratio of washing solution to fiber is between 30 to 150 parts liquid (pH 3 to 4) to 1 part fiber. Washing for 2 to 4 hours generally removes the surface chemical contamination and non-fibrous material (shot) which contributes to silica fiber devitrification. After washing, the fibers are rinsed 3 times at approximately the same liquid to fiber ratio for 10 to 15 minutes with deionized water, The pH is then about 6. Excess water is drained off leaving a ratio of 5 to 10 parts water to 1 part fiber. During this wash and all following procedures, great care must be taken to avoid contaminating the silica fibers. The use of polyethylene or stainless steel utensils and deionized water aids in avoiding such contamination. The washing procedure has little effect on the bulk chemical composition of the fiber. Its major function is the conditioning and dispersing of the silica fibers.

The alumina fibers are prepared by dispersing them in deionized water. They can be dispersed by mixing 10 to 40 parts water with 1 part fiber in a V-blender for 2 1/2 to 5 minutes. The time required is a function of the fiber length and diameter. In general, the larger the fiber, the more time required.

Generally, in order to manufacture low density ceramics, for example, densities below 12 lb/ft$^3$ ((192 kg/m$^3$)), the process includes the additional steps of:

(1) the addition of expendable carbon fibers in the casting process and/or other temporary support material; and
(2) firing the billet at about 1300° F. to remove the carbon fibers or other support material prior to the final firing at approximately 1600° F. or above.

When the dispersed silica fibers and dispersed alumina fibers are combined, the pH may be acidic, and if so, should be adjusted to neutral with ammonium hydroxide. The slurry should contain about 12 to about 25 parts water to about 1 part fiber. The slurry is mixed to a uniform consistency in a V-blender in 5 to 20 minutes. The boron nitride can be added at this point (2.85% by weight of the fibers) and mixed to a uniform consistency in a V-blender for an additional 5 to 15 minutes creating a Master Slurry. The preferred mixing procedure uses 15 parts water to 1 part fiber and the slurry is produced in about 20 minutes of mixing. At lower density formulations, expendable carbon fibers are used to give "green" strength to the billet prior to the final sintering. The percent of carbon fiber used varies greatly depending on the diameter, length and source of the fiber and the ultimate density of the material being produced. The percent of carbon fiber per dry weight of material should range between 1% and 10%. The source of the carbon fiber can take many forms including nylon, cellulose, and purified graphite based carbon in fibrous form. Carbon fibers added in the casting process are eliminated by firing the billets at 1350° F. prior to the final firing at 2450° F.

The master slurry is poured into a mold for pressing into the desired shape. The water is withdrawn rapidly and the resulting felt is compressed at 10 to 20 psi. Rapid removal of the water is required to prevent the fibers from separating. If graded properties are desired in the resultant material, the slurry can be allowed to settle and the fibers to partially separate before the removal of the water.

The final density of the finished ceramic is determined in part by the amount of compression placed on the felt, varying the wet molded dimension in relation to the fiber content. The ceramic has been prepared in densities ranging from about 0.05 to 0.48 g/cc. It can, however, be prepared in lower and higher densities.

After molding, the ceramic can be dried and fired by the following procedure. The ceramic is first dried in an oven for 18 hours; the temperature, initially 38° C., is raised at a rate of 11° C. per hour to 104° C., held there for 4 hours, raised again at a rate of 11° C. per hour to 150° C., and held there for 4 hours. The ceramic is taken directly from the drying oven, placed in the firing furnace, and fired. A temperature rise rate of 220° C. per hour or less is required in order to avoid cracking and warping in the case of a 15 cm×15 cm×7.5 cm block of material. For larger blocks, slower heating rates may be required. The maximum firing temperature may vary from 1200° C. to 1600° C. depending upon the fiber ratio used, amount of boron nitride, and the final density of the ceramic that is desired.

The temperature rise rate is chosen to permit relatively uniform temperatures to be achieved throughout the material during the process. A faster temperature rise rate causes non-uniform temperatures to be achieved throughout the ceramic during the process. A faster temperature rise rate causes non-uniform strength and density and may cause cracking. Longer or higher temperature firing results in higher shrinkage and related greater resistance to subsequent shrinkage, as well as a shorter lifetime to devitrification under cyclic exposures to high temperatures. The maximum firing temperature is dependent upon the fiber ratio used and the density of the composite desired. The firing time and maximum temperature are selected to allow sufficient shrinkage to achieve stabilization and fiber fusion while not allowing any devitrification. After firing, the ceramic may be machined to obtain any desired final dimensions.

Example 2

Preparation of Metal Particle Suspension

A suspension of metal particles may be formed by addition of metal particles to water, alcohol or a combination thereof followed by agitation of the water. Up to 25% by volume metal may be suspended in the water in the present example. Smaller proportions, such as up to 2%, 5%, 10%, 15% or 20% metal particles by volume are also possible. The proportion of metal particles in the water may be varied to affect ease of maintaining a suspension, amount of particles deposited in the ceramic, and proportion of ceramic void space filled with particles. Metal particles may require repeated or frequent agitation in order to remain in suspension.

In one embodiment, copper nanoparticles may be prepared, for example, as in U.S. Pat. No. 6,346,136 then suspended in water.

Example 3

Preparation of Hybrid Material

A hybrid material of the present invention may be prepared by placing a ceramic material of Example 1 in a chamber. A suspension of metal particles may be prepared according to Example 2. The particles should have an average diameter less than the average pore size of the ceramic. Preferably the average metal particle diameter will be less than two-thirds the average pore size of the ceramic.

The metal particle suspension may be poured into the ceramic and allowed to fill the chamber. The chamber may be agitated during or for some time after addition of the suspension. The ceramic may be allowed to remain undisturbed in the suspension for some time to allow the metal particles to settle in it.

The remaining suspension may then be drained from the bottom of the chamber and the ceramic dried. Metal particles will remain in the ceramic. If the particles are small in diameter compared to the average pore diameter of the ceramic, for instance no more than 1/10, they will tend to settle in the lower region of the ceramic and fill substantially all void space in that region. If the particles are larger, they will remain more evenly distributed throughout the ceramic, but may fill less void space.

After the remaining suspension has been removed, an electric current may be applied to the ceramic to melt the metal particles. Other heat sources may also be used to melt the particles. The method and speed of melting may affect the distribution of metal within the hybrid material as well as bonding between the metal and the ceramic.

Unsuitable portions of hybrid materials, such as regions with little metal content or uneven distribution may be removed, for example by machining.

All of the compositions and/or methods disclosed and claimed herein can be made and executed without undue experimentation in light of the present disclosure. While the compositions and methods of this invention have been described in terms of specific embodiments, it will be apparent to those of skill in the art that variations may be applied to the compositions and/or methods and in the steps or in the sequence of steps of the methods described herein without departing from the concept, spirit and scope of the invention. All such similar substitutes and modifications apparent to those skilled in the art are deemed to be within the spirit, scope and concept of the invention.

What is claimed is:

1. A method of making a hybrid material comprising:
   providing a porous ceramic with a matrix of interconnected void space wherein the ceramic includes exposed surfaces comprising at least 50% silicon dioxide prior to introducing metal particles into the void space;
   introducing a fluid comprising the metal particles into the porous ceramic such that the metal particles flow throughout the interconnected void space of the ceramic; and
   heating the metal particles to cause the metal particles present in the interconnected void space of the ceramic to react with oxygen of the silicon dioxide of the ceramic to form a covalent bond between the metal and the ceramic.

2. The method of claim 1, wherein the metal particles are heated by supplying an electric current to the metal particles.

3. The method of claim 1, wherein the ceramic comprises 100% silica.

4. The method of claim 1, wherein the ceramic comprises up to 50% cristobalite.

5. The method of claim 1, wherein the ceramic comprises up to 60% alumina.

6. The method of claim 1, wherein the ceramic includes exposed surfaces comprising titanium dioxide or platinum oxide prior to introducing the metal particles.

7. The method of claim 1, wherein the metal particles are selected from the group consisting of: Mg, Ca, Sc, Ti, Cr, Mn, Fe, Co, Ni, Cu, Zn, Pd, Ag, Cd, Pt, Au, any ionic forms thereof, and any combinations thereof.

8. The method of claim 1, wherein the metal particles comprise an alloy.

9. The method of claim 1, wherein the metal particles are microparticles.

10. The method of claim 1, wherein the metal particles are nanoparticles.

11. The method of claim 1, wherein the ceramic has an average pore size and the metal particles have an average diameter and wherein the average diameter of the metal particles is less than the average pore size of the ceramic.

12. The method of claim 10, wherein the average diameter of the metal particles is no greater then two thirds the average pore size of the ceramic.

13. The method of claim 1, wherein introducing metal particles into the matrix of interconnected void space comprises introducing a suspension of metal particles into the ceramic.

14. The method of claim 13, wherein the suspension of metal particles comprises alcohol, water or a combination thereof.

15. The method of claim 1, wherein heating the metal particles further comprises convection heating.

16. The method of claim 1, wherein the at least 50% of the void space is occupied by the metal.

17. The method of claim 1, wherein the metal comprises at least 50% of the hybrid material by weight.

18. The method of claim 1, wherein the metal comprises at least 50% of the hybrid material by volume.

19. The method of claim 1, wherein introducing a fluid comprising the metal particles into the porous ceramic such that the metal particles flow throughout the interconnected void space of the ceramic comprises:

surrounding the ceramic with the fluid comprising the metal particles, such that the fluid flows throughout the interconnected void space of the ceramic; and removing the ceramic from the fluid, wherein fluid that has flowed in the interconnected void space of the ceramic remains in the void space after removing the ceramic from the fluid.

* * * * *